(12) United States Patent
Rowe

(10) Patent No.: US 7,613,504 B2
(45) Date of Patent: Nov. 3, 2009

(54) SPECTROSCOPIC CROSS-CHANNEL METHOD AND APPARATUS FOR IMPROVED OPTICAL MEASUREMENTS OF TISSUE

(75) Inventor: Robert K. Rowe, Corrales, NM (US)

(73) Assignee: Lumidigm, Inc., Albuquerque, NM (US)

( * ) Notice: Subject to any disclaimer, the term of this patent is extended or adjusted under 35 U.S.C. 154(b) by 928 days.

(21) Appl. No.: 10/262,403

(22) Filed: Sep. 30, 2002

(65) Prior Publication Data

US 2003/0078504 A1    Apr. 24, 2003

Related U.S. Application Data

(63) Continuation-in-part of application No. 09/874,740, filed on Jun. 5, 2001.

(51) Int. Cl.
*A61B 6/00* (2006.01)
*A61B 5/00* (2006.01)

(52) U.S. Cl. .................. 600/476; 600/310; 600/473

(58) Field of Classification Search ............... 600/476, 600/310; 356/432; 250/341.7, 345; 382/115
See application file for complete search history.

(56) References Cited

U.S. PATENT DOCUMENTS

| | | |
|---|---|---|
| 3,508,830 A | 4/1970 | Hopkins et al. |
| 3,910,701 A | 10/1975 | Henderson et al. |
| RE29,008 E | 10/1976 | Ott |
| 4,035,083 A | 7/1977 | Woodriff et al. |
| 4,142,797 A | 3/1979 | Astheimer |
| 4,169,676 A | 10/1979 | Kaiser |
| 4,260,220 A | 4/1981 | Whitehead |
| 4,427,889 A | 1/1984 | Muller |
| 4,537,484 A | 8/1985 | Fowler et al. |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |

(Continued)

FOREIGN PATENT DOCUMENTS

EP    0 280 418 A1    8/1988

(Continued)

OTHER PUBLICATIONS

Bleyer, Anthony J. et al., "The Costs Of Hospitalizations Due To Hemodialysis Access Management," Nephrology News & Issues, pp. 19, 20 and 22, Jan. 1995.

(Continued)

*Primary Examiner*—Eric F Winakur
*Assistant Examiner*—Katherine L Fernandez
(74) *Attorney, Agent, or Firm*—Townsend, Townsend & Crew LLP

(57) ABSTRACT

According to the invention, a sampling system for spectroscopic measurements of a biological sample is disclosed. The sampling system includes a plurality of illumination points, a plurality of detection points, a memory, and a processor. Each of the plurality of illumination points is involved in at least two measurements of illumination through the biological sample. Each of the plurality of detection points is involved in at least two measurements of illumination through the biological sample. The memory stores a plurality of measurements. The processor determines a value from the plurality of measurements that is related to the biological sample.

40 Claims, 8 Drawing Sheets

U.S. PATENT DOCUMENTS

| | | | |
|---|---|---|---|
| 4,657,397 A | 4/1987 | Oehler et al. | |
| 4,661,706 A | 4/1987 | Messerschmidt et al. | |
| 4,684,255 A | 8/1987 | Ford | |
| 4,712,912 A | 12/1987 | Messerschmidt | |
| 4,730,882 A | 3/1988 | Messerschmidt | |
| 4,787,013 A | 11/1988 | Sugino et al. | |
| 4,787,708 A | 11/1988 | Whitehead | |
| 4,830,496 A | 5/1989 | Young | |
| 4,853,542 A | 8/1989 | Milosevic et al. | |
| 4,857,735 A | 8/1989 | Noller | |
| 4,859,064 A | 8/1989 | Messerschmidt et al. | |
| 4,866,644 A | 9/1989 | Shenk et al. | |
| 4,867,557 A | 9/1989 | Takatani et al. | |
| 4,882,492 A | 11/1989 | Schlager | |
| 4,883,953 A | 11/1989 | Koashi et al. | |
| 4,936,680 A | 6/1990 | Henkes et al. | |
| 4,944,021 A | 7/1990 | Hoshino et al. | |
| 4,975,581 A | 12/1990 | Robinson et al. | |
| 5,015,100 A | 5/1991 | Doyle | |
| 5,019,715 A | 5/1991 | Sting et al. | |
| 5,028,787 A | 7/1991 | Rosenthal et al. | |
| 5,051,602 A | 9/1991 | Sting et al. | |
| 5,068,536 A | 11/1991 | Rosenthal | |
| 5,070,874 A | 12/1991 | Barnes et al. | |
| 5,088,817 A * | 2/1992 | Igaki et al. | 356/71 |
| 5,158,082 A | 10/1992 | Jones | |
| 5,163,094 A | 11/1992 | Prokoski et al. | |
| 5,178,142 A | 1/1993 | Harjunmaa et al. | |
| 5,179,951 A | 1/1993 | Knudson | |
| 5,204,532 A | 4/1993 | Rosenthal | |
| 5,222,495 A | 6/1993 | Clarke et al. | |
| 5,222,496 A | 6/1993 | Clarke et al. | |
| 5,223,715 A | 6/1993 | Taylor | |
| 5,225,678 A | 7/1993 | Messerschmidt | |
| 5,230,702 A | 7/1993 | Lindsay et al. | |
| 5,237,178 A | 8/1993 | Rosenthal et al. | |
| 5,243,546 A | 9/1993 | Maggard | |
| 5,257,086 A | 10/1993 | Fateley et al. | |
| 5,267,152 A | 11/1993 | Yang et al. | |
| 5,268,749 A | 12/1993 | Weber et al. | |
| 5,291,560 A | 3/1994 | Daugman | |
| 5,299,570 A | 4/1994 | Hatschek | |
| 5,303,026 A | 4/1994 | Strobl et al. | |
| 5,311,021 A | 5/1994 | Messerschmidt | |
| 5,313,941 A | 5/1994 | Braig et al. | |
| 5,321,265 A | 6/1994 | Block | |
| 5,331,958 A | 7/1994 | Oppenheimer | |
| 5,348,003 A | 9/1994 | Caro | |
| 5,351,686 A | 10/1994 | Steuer et al. | |
| 5,355,880 A | 10/1994 | Thomas et al. | |
| 5,360,004 A | 11/1994 | Purdy et al. | |
| 5,361,758 A | 11/1994 | Hall et al. | |
| 5,366,903 A | 11/1994 | Lundsgaard et al. | |
| 5,372,135 A | 12/1994 | Mendelson et al. | |
| 5,379,764 A | 1/1995 | Barnes et al. | |
| 5,402,778 A | 4/1995 | Chance | |
| 5,405,315 A | 4/1995 | Khuri et al. | |
| 5,419,321 A | 5/1995 | Evans | |
| 5,435,309 A | 7/1995 | Thomas et al. | |
| 5,441,053 A | 8/1995 | Lodder et al. | |
| 5,452,723 A | 9/1995 | Wu et al. | |
| 5,459,317 A | 10/1995 | Small et al. | |
| 5,459,677 A | 10/1995 | Kowalski et al. | |
| 5,460,177 A | 10/1995 | Purdy et al. | |
| 5,483,335 A | 1/1996 | Tobias | |
| 5,494,032 A | 2/1996 | Robinson et al. | |
| 5,505,726 A | 4/1996 | Meserol | |
| 5,507,723 A | 4/1996 | Keshaviah | |
| 5,515,847 A | 5/1996 | Braig et al. | |
| 5,518,623 A | 5/1996 | Keshaviah et al. | |
| 5,523,054 A | 6/1996 | Switalski et al. | |
| 5,533,509 A | 7/1996 | Koashi et al. | |
| 5,537,208 A | 7/1996 | Bertram et al. | |
| 5,539,207 A | 7/1996 | Wong | |
| 5,552,997 A | 9/1996 | Massart | |
| 5,559,504 A | 9/1996 | Itsumi et al. | |
| 5,596,992 A | 1/1997 | Haaland et al. | |
| 5,606,164 A | 2/1997 | Price et al. | |
| 5,630,413 A | 5/1997 | Thomas et al. | |
| 5,636,633 A | 6/1997 | Messerschmidt et al. | |
| 5,655,530 A | 8/1997 | Messerschmidt | |
| 5,672,864 A | 9/1997 | Kaplan | |
| 5,672,875 A | 9/1997 | Block et al. | |
| 5,677,762 A | 10/1997 | Ortyn et al. | |
| 5,681,273 A | 10/1997 | Brown | |
| 5,708,593 A | 1/1998 | Saby et al. | |
| 5,719,399 A | 2/1998 | Alfano et al. | |
| 5,719,950 A | 2/1998 | Osten et al. | |
| 5,724,268 A | 3/1998 | Sodickson et al. | |
| 5,737,439 A | 4/1998 | Lapsley et al. | |
| 5,743,262 A | 4/1998 | Lepper, Jr. et al. | |
| 5,747,806 A | 5/1998 | Khalil | |
| 5,750,994 A | 5/1998 | Schlager | |
| 5,751,835 A | 5/1998 | Topping et al. | |
| 5,761,330 A | 6/1998 | Stoianov et al. | |
| 5,782,755 A | 7/1998 | Chance et al. | |
| 5,792,050 A | 8/1998 | Alam et al. | |
| 5,792,053 A | 8/1998 | Skladnev et al. | |
| 5,793,881 A | 8/1998 | Stiver et al. | |
| 5,796,858 A | 8/1998 | Zhou et al. | |
| 5,808,739 A | 9/1998 | Turner et al. | |
| 5,818,048 A | 10/1998 | Sodickson et al. | |
| 5,823,951 A | 10/1998 | Messerschmidt | |
| 5,828,066 A | 10/1998 | Messerschmidt | |
| 5,830,132 A | 11/1998 | Robinson | |
| 5,830,133 A | 11/1998 | Osten et al. | |
| 5,850,623 A | 12/1998 | Carman, Jr. et al. | |
| 5,853,370 A | 12/1998 | Chance et al. | |
| 5,857,462 A | 1/1999 | Thomas et al. | |
| 5,860,421 A | 1/1999 | Eppstein et al. | |
| 5,867,265 A | 2/1999 | Thomas | |
| 5,886,347 A | 3/1999 | Inoue et al. | |
| 5,902,033 A | 5/1999 | Levis et al. | |
| 5,914,780 A | 6/1999 | Turner et al. | |
| 5,929,443 A | 7/1999 | Alfano et al. | |
| 5,933,792 A | 8/1999 | Anderson et al. | |
| 5,935,062 A | 8/1999 | Messerschmidt et al. | |
| 5,945,676 A | 8/1999 | Khalil | |
| 5,949,543 A | 9/1999 | Bleier et al. | |
| 5,957,841 A | 9/1999 | Maruo et al. | |
| 5,961,449 A | 10/1999 | Toida et al. | |
| 5,963,319 A | 10/1999 | Jarvis et al. | |
| 5,987,346 A | 11/1999 | Benaron et al. | |
| 5,999,637 A | 12/1999 | Toyoda et al. | |
| 6,005,722 A | 12/1999 | Butterworth et al. | |
| 6,016,435 A | 1/2000 | Maruo et al. | |
| 6,025,597 A | 2/2000 | Sterling et al. | |
| 6,026,314 A | 2/2000 | Amerov et al. | |
| 6,028,773 A | 2/2000 | Hundt | |
| 6,031,609 A | 2/2000 | Funk et al. | |
| 6,034,370 A | 3/2000 | Messerschmidt | |
| 6,040,578 A | 3/2000 | Malin et al. | |
| 6,041,247 A | 3/2000 | Weckstrom et al. | |
| 6,041,410 A | 3/2000 | Hsu et al. | |
| 6,043,492 A | 3/2000 | Lee et al. | |
| 6,044,285 A | 3/2000 | Chaiken et al. | |
| 6,045,502 A | 4/2000 | Eppstein et al. | |
| 6,046,808 A | 4/2000 | Fateley | |
| 6,049,727 A | 4/2000 | Crothall | |
| 6,056,738 A | 5/2000 | Marchitto et al. | |
| 6,057,925 A | 5/2000 | Anthon | |
| 6,061,581 A | 5/2000 | Alam et al. | |
| 6,061,582 A | 5/2000 | Small et al. | |
| 6,066,847 A | 5/2000 | Rosenthal | |

| | | | |
|---|---|---|---|
| 6,069,689 A | 5/2000 | Zeng et al. | |
| 6,070,093 A | 5/2000 | Oosta et al. | |
| 6,073,037 A | 6/2000 | Alam et al. | |
| 6,088,605 A | 7/2000 | Griffith et al. | |
| 6,088,607 A | 7/2000 | Diab et al. | |
| 6,097,035 A | 8/2000 | Belongie et al. | |
| 6,100,811 A | 8/2000 | Hsu et al. | |
| 6,115,484 A | 9/2000 | Bowker et al. | |
| 6,115,673 A | 9/2000 | Malin et al. | |
| 6,122,042 A | 9/2000 | Wunderman et al. | |
| 6,122,394 A | 9/2000 | Neukermans et al. | |
| 6,122,737 A | 9/2000 | Bjorn et al. | |
| 6,125,192 A | 9/2000 | Bjorn et al. | |
| 6,141,101 A | 10/2000 | Bleier et al. | |
| 6,147,749 A | 11/2000 | Kubo et al. | |
| 6,148,094 A | 11/2000 | Kinsella | |
| 6,152,876 A | 11/2000 | Robinson et al. | |
| 6,154,658 A | 11/2000 | Caci | |
| 6,157,041 A | 12/2000 | Thomas et al. | |
| 6,159,147 A | 12/2000 | Lichter et al. | |
| 6,172,743 B1 | 1/2001 | Kley et al. | |
| 6,175,407 B1 | 1/2001 | Sartor | |
| 6,181,414 B1 | 1/2001 | Raz et al. | |
| 6,181,958 B1 | 1/2001 | Steuer et al. | |
| 6,188,781 B1 | 2/2001 | Brownlee | |
| 6,212,424 B1 | 4/2001 | Robinson | |
| 6,226,541 B1 | 5/2001 | Eppstein et al. | |
| 6,230,034 B1 | 5/2001 | Messerschmidt et al. | |
| 6,240,306 B1 | 5/2001 | Rohrscheib et al. | |
| 6,240,309 B1 | 5/2001 | Yamashita et al. | |
| 6,241,663 B1 | 6/2001 | Wu et al. | |
| 6,256,523 B1 | 7/2001 | Diab et al. | |
| 6,272,367 B1 | 8/2001 | Chance | |
| 6,280,381 B1 | 8/2001 | Malin et al. | |
| 6,282,303 B1 | 8/2001 | Brownlee | |
| 6,285,895 B1 | 9/2001 | Ristolainen et al. | |
| 6,292,576 B1 | 9/2001 | Brownlee | |
| 6,301,815 B1 | 10/2001 | Sliwa | |
| 6,304,767 B1 | 10/2001 | Soller et al. | |
| 6,307,633 B1 | 10/2001 | Mandella et al. | |
| 6,309,884 B1 | 10/2001 | Cooper et al. | |
| 6,317,507 B1 | 11/2001 | Dolfing | |
| 6,324,310 B1 | 11/2001 | Brownlee | |
| 6,330,346 B1 | 12/2001 | Peterson et al. | |
| 6,404,904 B1 | 6/2002 | Einighammer et al. | |
| 6,483,929 B1 | 11/2002 | Murakami et al. | |
| 6,504,614 B1 | 1/2003 | Messerschmidt et al. | |
| 6,560,352 B2 | 5/2003 | Rowe et al. | |
| 6,574,490 B2* | 6/2003 | Abbink et al. | 600/316 |
| 6,628,809 B1 | 9/2003 | Rowe et al. | |
| 6,741,729 B2 | 5/2004 | Bjorn et al. | |
| 6,799,275 B1 | 9/2004 | Bjorn | |
| 6,816,605 B2 | 11/2004 | Rowe et al. | |
| 6,859,275 B2* | 2/2005 | Fateley et al. | 356/330 |
| 2002/0009213 A1* | 1/2002 | Rowe et al. | 382/115 |
| 2002/0171834 A1 | 11/2002 | Rowe et al. | |
| 2002/0183624 A1 | 12/2002 | Rowe et al. | |
| 2003/0078504 A1 | 4/2003 | Rowe | |
| 2004/0047493 A1 | 3/2004 | Rowe et al. | |
| 2004/0240712 A1 | 12/2004 | Rowe et al. | |

FOREIGN PATENT DOCUMENTS

| | | |
|---|---|---|
| EP | 0 426 358 B1 | 5/1991 |
| EP | 0 449 335 A2 | 10/1991 |
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 164 A2 | 2/1999 |
| EP | 0 897 691 A2 | 2/1999 |
| EP | 0 317 121 B1 | 5/1999 |
| EP | 0 924 656 A2 | 6/1999 |
| EP | 0 982 583 A1 | 3/2000 |
| EP | 0 990 945 A1 | 4/2000 |
| JP | 3016160 | 1/1991 |
| JP | 10-127585 | 5/1998 |
| JP | 2001-112742 | 4/2001 |
| WO | WO 92/00513 A1 | 1/1992 |
| WO | WO 92/17765 A1 | 10/1992 |
| WO | WO 93/00855 A1 | 1/1993 |
| WO | WO 93/07801 A1 | 4/1993 |
| WO | WO 95/22046 A1 | 8/1995 |
| WO | WO 97/23159 A1 | 7/1997 |
| WO | WO 97/27800 A1 | 8/1997 |
| WO | WO 97/28437 A1 | 8/1997 |
| WO | WO 97/28438 A1 | 8/1997 |
| WO | WO 98/01071 A1 | 1/1998 |
| WO | WO 98/37805 A1 | 9/1998 |
| WO | WO 98/40723 A1 | 9/1998 |
| WO | WO 99/09395 A1 | 2/1999 |
| WO | WO 99/37203 A2 | 7/1999 |
| WO | WO 99/43255 A1 | 9/1999 |
| WO | WO 99/46731 A1 | 9/1999 |
| WO | WO 99/55222 A1 | 11/1999 |
| WO | WO 99/56616 A1 | 11/1999 |
| WO | WO 00/30530 | 6/2000 |
| WO | WO 01/15596 A1 | 3/2001 |
| WO | WO 01/18332 A1 | 3/2001 |
| WO | WO 01/20538 | 3/2001 |
| WO | WO 01/27882 A2 | 4/2001 |
| WO | WO 01/52180 A1 | 7/2001 |
| WO | WO 01/52726 A1 | 7/2001 |
| WO | WO 01/53805 A1 | 7/2001 |
| WO | WO 02/084605 A2 | 10/2002 |
| WO | WO 02/099393 A2 | 12/2002 |

OTHER PUBLICATIONS

Demos, S. G. et al., "Optical Fingerprinting Using Polarisation Contrast Improvement," Electronics Letters, vol. 33, No. 7, pp. 582-584; Mar. 27, 1997.

Depner, Thomas A. et al., "Clinical Measurement Of Blood Flow In Hemodialysis Access Fistulae And Grafts By Ultrasound Dilution," Division of Nephrology, University of California, pp. M745-M748, published on or before Oct. 30, 1997.

Fresenius USA, "Determination Of Delivered Therapy Through Measurement Of Effective Clearance," 2 pages, Dec. 1994.

Hakim, Raymond M. et al., "Effects Of Dose Of Dialysis On Morbidity And Mortality," American Journal of Kidney Diseases, vol. 23, No. 5, pp. 661-669, May 1994.

Jacobs, Paul et al., "A Disposable Urea Sensor For Continuous Monitoring Of Hemodialysis Efficiency," ASAIO Journal, pp. M353-M358, 1993.

Keshaviah, Prakash R. et al., "On-Line Monitoring Of The Delivery Of The Hemodialysis Prescription," Pediatric Nephrology, vol. 9, pp. S2-S8, 1995.

Krivitski, Nikolai M., "Theory And Validation Of Access Flow Measurement By Dilution Technique During Hemodialysis," Kidney International, vol. 48, pp. 244-250, 1995.

Ripley, B. D., "Chapter 3—Linear Discriminant Analysis," Pattern Recognition And Neural Networks, pp. 3 cover pp. and 91-120; 1996.

Ronco, C. et al., "On-Line Urea Monitoring : A Further Step Towards Adequate Dialysis Prescription And Delivery," The International Journal of Artificial Organs, vol. 18, No. 9, pp. 534-543, 1995.

Sherman, Richard A., "Chapter 4—Recirculation In The Hemodialysis Access," Principles and Practice of Dialysis, pp. 2 cover pp. and 38-46, 1994.

Sherman, Richard A., "The Measurement Of Dialysis Access Recirculation," American Journal of Kidney Diseases, vol. 22, No. 4, pp. 616-621, Oct. 1993.

Steuer, Robert R. et al., "A New Optical Technique For Monitoring Hematocrit And Circulating Blood Volume: Its Application In Renal Dialysis," Dialysis & Transplantation, vol. 22, No. 5, pp. 260-265, May 1993.

Webb, Paul, "Temperatures Of Skin, Subcutaneous Tissue, Muscle And Core In Resting Men In Cold, Comfortable And Hot Conditions," European Journal of Applied Physiology, vol. 64, pp. 471-476, 1992.

Zavala, Albert et al., "Using Fingerprint Measures To Predict Other Anthropometric Variables," Human Factors, vol. 17, No. 6, pp. 591-602, 1975.

Anderson, C. E. et al., "Fundamentals of Calibration Transfer Through Procrustes Analysis," Appln. Spectros., vol. 53, No. 10 (1999) p. 1268-1276.

Ashboum, Julian, Biometrics; Advanced Identity Verification, Springer, 2000, pp. 63-64).

Blank, T.B. et al., "Transfer of Near-Infrared Multivariate Calibrations Without Standards," Anal. Chem., vol. 68 (1996) p. 2987.

Brasunas John C. et al., "Uniform Time-Sampling Fourier Transform Spectroscopy," Applied Optics, vol. 36, No. 10, Apr. 1, 1997, pp. 2206-2210.

Brault, James W., "New Approach to High-Precision Fourier Transform Spectrometer Design," Applied Optics, Vo. 35, No. 16, Jun. 1, 1996, pp. 2891-2896.

Brochure entitled "Improve the Clinical Outcome of Every Patient", In Line Diagnostics, published on or before Oct. 30, 1997, 2 pages.

Cassarly, W.J. et al., "Distributed Lighting Systems: Uniform Light Delivery," Source Unknown, pp. 1698-1702.

Chang, Chong-Min et al., "An Uniform Rectangular Illuminating Optical System for Liquid Crystal Light Valve Projectors," Euro Display '96 (1996) pp. 257-260.

Coyne, Lawrence J. et al., "Distributive Fiber Optic couplers Using Rectangular Lightguides as Mixing Elements," (Information Gatekeepers, Inc. Brookline, MA, 1979) pp. 160-164.

de Noord, Onno E., "Multivariate Calibration Standardization," Chemometrics and intelligent Laboratory Systems 25, (1994) pp. 85-97.

Despain, Alvin M. et al., "A Large-Aperture Field-Widened Interferometer-Spectrometer for Airglow Studies," Aspen International Conference on Fourier Spectroscopy, 1970, pp. 293-300.

Faber, Nicolaas, "Multivariate Sensitivity for the Interpretation of the Effect of Spectral Pretreatment Methods on Near-Infrared Calibration Model Predictions," Analytical Chemistry, vol. 71, No. 3, Feb. 1, 1999, pp. 557-565.

Geladi, Paul et al., A Multivariate NIR Study of Skin Alterations in Diabetic Patients as Compared to Control Subjects, J. Near Infrared Spectrosc., vol. 8 (2000) pp. 217-227.

Haaland, David M. et al. "Reagentless Near-Infrared Determination of Glucose in Whole Blood Using Multivariate Calibration," Applied Spectroscopy, vol. 46, No. 10 (1992) pp. 1575-1578.

Harwit, M. et al., "Chapter 5—Instrumental Considerations" Hadamard Transform Optics, Academic Press (1979) pp. 109-145.

Heise H. Michael et al., "Near-Infrared Reflectance Spectroscopy for Noninvasive Monitoring of Metabolites," Clin. Chem. Lab. Med. 2000, 38(2) (2000) pp. 137-145.

Heise, H.M. "Non-Invasive Monitoring of Metabolites Using Near Infrared Spectroscopy: State of the Art," Horm. Metab. Res., vol. 28 (1996) pp. 527-534.

Heise, H.M. et al., "Near Infrared Spectrometric Investigation of Pulsatile Blood Flow for Non Invasive Metabolite Monitoring," CP430, Fourier Transform Spectroscopy: 11th International Conference, (1998) pp. 282-285.

Heise, H.M. et al., "Noninvasive Blood Glucose Sensors Based on Near-Infrared Spectroscopy," Artif Organs, vol. 18, No. 6 (1994) pp. 1-9.

Hopkins, George W. et al., "In-vivo NIR Diffuse-reflectance Tissue Spectroscopy of Human Subjects," SP1E, vol. 3597, Jan. 1999, pp. 632-641.

Jagemann, Kay-Uwe et al. "Application of Near-Infrared Spectroscopy for Non-Invasive Determination of Blood/Tissue Glucose Using Neural Networks," Zeitschrift for Physikalische Chemie, Bd.191, S. 179-190 (1995).

Khalil, Omar S., "Spectroscopic and Clinical Aspects of Noninvasive Glucose Measurements," Clinical Chemistry, 45:2 (1999) pp. 165-177.

Kohl, Matthias et al., "The Influence of Glucose Concentration Upon the Transport of Light in Tissue-simulating Phantoms," Phys. Med. Biol., vol. 40 (1995) pp. 1267-1287.

Korte, E.H. et al., "Infrared Diffuse Reflectance Accessory for Local Analysis on Bulky Samples," Applied Spectroscopy, vol. 42, No. 1, Jan. 1988, pp. 38-43.

Kumar, G. et al., "Optimal Probe Geometry for Near-Infrared Spectroscopy of Biological Tissue," Applied Spectroscopy, vol. 36 (1997) p. 2286.

Lorber, Avraham et al., "Local Centering in Multivariate Calibration," Journal of Chemometrics, vol. 10 (1996) pp. 215-220.

Lorber, Avraham et al., "Net Analyte Signal Calculation in Multivariate Calibration," Analytical Chemistry, vol. 69, No. 8, Apr. 15, 1997, pp. 1620-1626.

Marbach, R. et al. "Noninvasive Blood Glucose Assay by Near-Infrared Diffuse Reflectance Spectroscopy of the Human Inner Lip," Applied Spectroscopy, vol. 47, No. 7 (1993) pp. 875-881.

Marbach, R. et al. "Optical Diffuse Reflectance Accessory for Measurements of Skin Tissue by Near-Infrared Spectroscopy," Applied Optics, vol. 34, No. 4, Feb. 1, 1995, pp. 610-621.

Martens, Harald et al., Updating Multivariate Calibrations of Process NIR Instruments, Adv. Instru. Control (1990) pp. 371-381.

McIntosh, Bruce C. et al. "Quantitative Reflectance Spectroscopy in the Mid-IR", 16' Annual FACSS Conference, Oct. 1989.

Offner, A., "New Concepts in Projection Mask Aligners," Optical Engineering, vol. 14, No. 2, Mar.-Apr. 1975, pp. 130-132.

Osborne, B.G. et al., "Optical Matching of Near Infrared Reflectance Monochromator Instruments for the Analysis of Ground and Whole Wheat," J. Near Infrared Spectrosc., vol. 7 (1999) p. 167.

Ozdemir, d. et al., "Hybrid Calibration Models: An Alternative to Calibration Transfer," Applied Spectros., vol. 52, No. 4, 1998, pp. 599-603.

Powell, J.R. et al, "An Algorithm for the Reproducible Spectral Subtraction of Water from the FT IR Spectra of Proteins in Dilute Solutions and Adsorbed Monolayers," Applied Spectroscopy, vol. 40, No. 3 (1986) pp. 339-344.

Robinson, M. Ries et al., "Noninvasive Glucose Monitoring in Diabetic Patients: A Preliminary Evaluation," Clinical Chemistry, vol. 38, No. 9 (1992) pp. 1618-1622.

Royston, David D. et al., "Optical Properties of Scattering and Absorbing Materials Used in the Development of Optical Phantoms at 1064 NM," Journal of Biomedical Optics, vol. 1, No. 1, Jan. 1996, pp. 110-116.

Rutan, Sarah C. et al., "Correction for Drift in Multivariate Systems Using the Kalman Filter," Chemometrics and Intelligent Laboratory Systems 35, (1996) pp. 199-211.

Salit, M.L. et al., "Heuristic and Statistical Algorithms for Automated Emission Spectral Background Intensity Estimation," Applied Spectroscopy, vol. 48, No. 8 (1994) pp. 915-925.

Saptari, Vidi Alfandi, "Analysis, Design and Use of a Fourier-Transform Spectrometer for Near Infrared Glucose Absorption Measurement," (Massachusetts Institute of Technology, 1999) pp. 1-76.

Schmitt, J.M. et al., "Spectral Distortions in Near-Infrared Spectroscopy of Turbid Materials," Applied Spectroscopy, No. 50 (1996) p. 1066.

Shroder, Robert, Slides from MicroPac Forum Presentation, Current performance results, May 11, 2000; slides 2,4,14.

Sjoblom, J. et al., "An Evaluation of Orthogonal Signal correction Applied to Calibration Transfer of Near Infrared Spectra," Chemom & Intell Lab. Systems, vol. 44 (1998) p. 229-244.

Steel, W.H., "Interferometers for Fourier Spectroscopy," Aspen International Conference on Fourier Spectroscopy, (1970) pp. 43-53.

Sternberg R.S. et al., "A New Type of Michelson Interference Spectrometer," Sci. Instrum., vol. 41 (1964) pp. 225-226.

Stork, Chris L. et al., "Weighting Schemes for Updating Regression Models—a Theoretical Approach," Chemometrics and Intelligent Laboratory Systems 48, (1999) pp. 151-166.

Sum, Stephen T. et al., "Standardization of Fiber-Optic Probes for Near-Infrared Multivariate Calibrations," Applied Spectroscopy, vol. 52, No. 6 (1998) pp. 869-877.

Swierenga, H. et al., "Comparison of Two Different Approaches Toward Model Transferability in NIR Spectroscopy," Applied Spectroscopy, vol. 52, No. 1 (1998) pp. 7-16.

Swierenga, H. et al., "Improvement of PLS Model Transferability by Robust Wavelength Selection," Chemometrics and Intelligent Laboratory Systems, vol. 41 (1998) pp. 237-248.

Swierenga, H. et al., "Strategy for Constructing Robust Multivariate Calibration Models," Chemometrics and Intelligent Laboratory Systems, vol. 49, (1999) pp. 1-17.

Teijido, J.M. et al., "Design of a Non-conventional Illumination System Using a Scattering Light Pipe," SPIE, Vo. 2774 (1996) pp. 747-756.

Teijido, J.M. et al., "Illumination Light Pipe Using Micro-Optics as Diffuser," SPIE, vol. 2951 (1996) pp. 146-155.

Thomas, Edward V. et al., "Development of Robust Multivariate Calibration Models," Technometrics, vol. 42, No. 2, May 2000, pp. 168-177.

Tipler, Paul A., Physics, Second Edition, Worth Publishers, Inc., Chapter 34, Section 34-2, Nov. 1983, pp. 901-908.

Wang, Y-D. et al., "Calibration Transfer and Measurement Stability of Near-Infrared Spectrometers," Appl. Spectros., vol. 46, No. 5 (1992) pp. 764-771.

Wang, Y-D. et al., "Improvement of Multivariate Calibration Through Instrument Standardization," Anal. Chem., vol. 64 (1992) pp. 562-564.

Wang, Z., "Additive Background Correction in Multivariate Instrument Standardization," Anal. Chem., vol. 67 (1995) pp. 2379-2385.

Ward, Kenneth J. et al., "Post-Prandial Blood Glucose Determination by Quantitative Mid-Infrared Spectroscopy," Applied Spectroscopy, vol. 46, No. 6 (1992) pp. 959-965.

Whitehead, L.A. et al., "High-efficiency Prism Light Guides with Confocal Parabolic Cross Sections," Applied Optics, vol. 37, No. 22 (1998) pp. 5227-5233.

Bantle, John P. et al., "*Glucose measurement in patients with diabetes mellitus with dermal interstitial fluid*", Copyright © 1997 by Mosby-Year Book, Inc., pp. 436-441, vol. 130, No. 4.

Berkoben et al., "Vascular Access for Hemodialysis", *Clinical Dialysis*, published on or before Oct. 30, 1997, 20 pages.

Daugirdas et al., "*Comparison of Methods to Predict the Equilibrated Kt/V (eKt/N) in the Hemo Study*", National Institutes of Health, NIDDK, Bethesda, MD, Aug. 20, 1996.

Marbach, Ralf, "*Measurement Techniques for IR Spectroscopic Blood Glucose Determination,* " (1994) pp. 1-158.

Mardia, K.V. et al., "*Multivariate Analysis*", Academic Press (1979) pp. 300-325.

Nichols, et al., "*Design and Testing of a White-Light, Steady-State Diffuse Reflectance Spectrometer for Determination of Optical Properties of Highly Scattering Systems,*" Applied Optics, Jan. 1, 1997, 36(1), pp. 93-104.

Service, F. John et al., "Dermal Interstitial Glucose as an Indicator of Ambient Glycemia," *Diabetes Care*, vol. 20, No. 9, Sep. 1997, 9 pages.

* cited by examiner

SPECTROSCOPIC CROSS-CHANNEL METHOD AND APPARATUS FOR IMPROVED OPTICAL MEASUREMENTS OF TISSUE

This application is a continuation-in-part of U.S. patent application Ser. No. 09/874,740, filed Jun. 5, 2001, entitled "Apparatus And Method Of Biometric Determination Using Specialized Optical Spectroscopy Systems," which is incorporated by reference in its entirety.

This application is related to U.S. patent application Ser. No. 09/415,594, filed Oct. 8, 1999, entitled "Apparatus and Method for Identification of Individuals by Near-Infrared Spectrum"; and U.S. patent application Ser. No. 09/832,534, filed Apr. 11, 2001, entitled "Apparatus and Method of Biometric Identification or Verification of Individuals Using Optical Spectroscopy"; which are all incorporated by reference in their entirety.

FIELD OF THE INVENTION

This invention generally relates to the field of optical measurements of tissue for applications including spectral biometrics and noninvasive analyte measurements.

BACKGROUND OF THE INVENTION

Optical systems are applied to measure biological media for a variety of purposes. Some of these systems are used for biometric purposes, for example, to read fingerprints or perform retinal scans. There are also medical uses for optical systems such as measuring the pulse or blood oxygenation of a patient. Biological media is difficult to measure accurately. Some of the optical systems attempt to mitigate the adverse effects of various artifacts at the optical interface to more accurately measure the biological media. Artifacts in biometric applications can result in false positive or negative results. Medical applications may have unacceptable error margins where the artifacts cannot be overcome.

BRIEF DESCRIPTION OF THE DRAWINGS

The present invention is described in conjunction with the appended figures.

Figure 1:
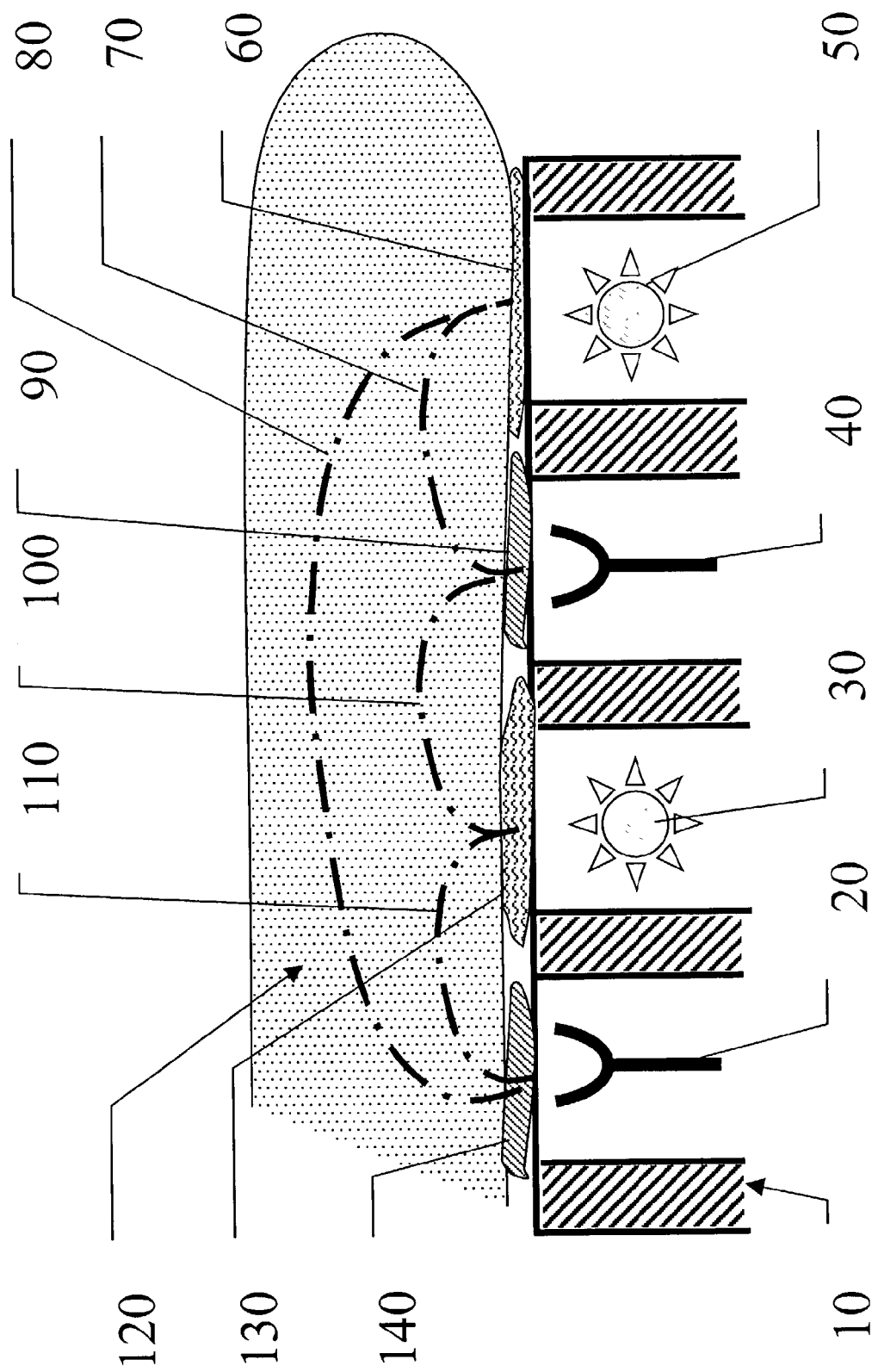
FIG. 1 is a diagram of a side view of an embodiment of a cross-channel spectroscopic sampling system.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE PREFERRED EMBODIMENT

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

In some embodiments, optical systems are applied to measure biological media for a variety of purposes. Optical spectrometers are used to make a variety of measurements on skin and underlying tissue. Spectroscopic systems are used for performing in vivo noninvasive measurements of a variety of analytes such as glucose, alcohol, blood gases, oxygen saturation and tissue hemoglobin, as well as the use of similar technology for disease screening and determination for cancer, diabetes and other such medical conditions.

In some embodiments, the present invention provides a method and apparatus that reduce the effects of artifacts from, for example, tissue heterogeneity, tissue topology, topical contamination, and sampler defects. Reducing these effects may result in: improved spectroscopic measurements of biological media for applications such as noninvasive analyte measurements, for example, glucose, oxygen saturation, tissue hemoglobin, alcohol, blood gases etc.; improved disease screening for medical conditions such as cancer and diabetes; and improved performance of spectral biometric systems carrying out biometric tasks such as identification, identity verification, and determination of age, gender, liveness and/or authenticity of the sample of biological media.

In one embodiment, the present invention includes illumination points and detection points. The illumination and detection points are arranged to provide a well-conditioned pathlength distribution matrix through the sample, and a means to measure the intensity of each wavelength of light for each of source-detector pair.

An embodiment of a method for improved spectroscopic sampling of biological media according to the present invention includes acquiring data from a sampler with illumination points and detection points. The illumination and detection points are arranged to provide a well-conditioned pathlength distribution matrix through the sample. The intensity of each wavelength of light is measured for each of the source-detector pairs and record the resulting data. Operations are preformed on the resulting data with a mathematical algorithm that can compensate for artifacts in the optical interface with the biological media.

In one embodiment, the present invention provides a sampling system for spectroscopic measurements of a biological sample. The sampling system includes a plurality of illumination points, a plurality of detection points, a memory, and a processor. Each of the plurality of illumination points is involved in at least two measurements of illumination through the biological sample. Each of the plurality of detection points is involved in at least two measurements of illumination through the biological sample. The memory stores a plurality of measurements. The processor determines a value from the plurality of measurements that is related to the biological sample.

In another embodiment, the present invention provides a method of performing spectroscopic determinations on a biological sample. Included in a sampling system are a plurality of illumination points and a plurality of detection points. In one step, illumination produced by each of the plurality of illumination points is measured a plurality of times. Illumination incident on each of the plurality of detection points is also measured a plurality of times. A value for the biological sample from data can be determined from these measurements.

In yet another embodiment, the present invention provides a sampler for spectroscopic measurements of a biological sample. The sampler includes a first illumination point, a second illumination point, a first detection point, and a second detection point. The first illumination point illuminates at least two detection points with measurable radiation. The second illumination point illuminates at least two detection points with measurable radiation. The first detection point receives measurable radiation from at least two illumination points. The second detection point receives measurable radiation from at least two illumination points. The first illumination point, the second illumination point, the first detection point, the second detection point are configured to operatively engage the biological sample.

To perform optical spectroscopic measurements of tissue absorbance, scatter, fluorescence, etc. for optical spectroscopic measurement of tissue, illumination light passes through the surface of the tissue. For purposes of this invention, the term "light" is used to refer to electromagnetic radiation with a wavelength range from 350 nm to 10 µm, spanning the very near ultraviolet, the visible, the near infrared and the mid-infrared spectral regions. Once the illumination light passes into the tissue, a portion of the illumination light can then be collected by a spectroscopic system after it passes through the tissue in a transmission configuration or is scattered back out of the tissue in a diffuse reflectance configuration. In either configuration, the light passes through the surface of the tissue a second time before being detected, measured and recorded by the spectroscopic system. In general, such measurements can be made in vivo on living tissue, in which case the light has to pass into or through the skin to get to the underlying tissue, or the measurements can be made ex vivo on extracted or excised samples or other forms of biological media. For simplicity, this document will describe aspects of the invention as they relate to in vivo spectroscopic measurements but those skilled in the art will appreciate the extension to ex vivo and other biological measurements are within the scope of the invention.

The term "sampler" is used in this document to refer to an apparatus that transmits light into the skin and collects the light after passing through the skin, regardless of how these functions are implemented (e.g., by separate components or apparatuses, or using a single apparatus). The sampler can be in physical contact with the skin surface or it might be physically separated with an air gap or another medium occupying the space between the skin and the sampler. In either case, the region in close proximity to the illuminated skin surface as well as the region around the skin surface over which light is appreciably collected, as well as the corresponding regions of the sampler apparatus, will collectively be referred to as the "optical interface" between the skin or surface of the biological sample and the sampler.

The optical interface defines a region of the optical path that is particularly prone to artifacts that can affect the resulting spectroscopic measurements. Sources of the artifacts include effects such as the uneven surface topology of the skin and poor optical coupling between the sampler and the skin, which can cause variations in the detected signal. Differences in tissue composition in close proximity to the optical interface can affect the detected signal. If the tissue being sampled moves relative to the sampler while taking measurements, then motion artifacts can be introduced due to changes in the optical interface. Topical contaminants on the skin surface or the sampler surface such as inks, dirt, lotions, etc can affect the optical signal.

Elements of a cross-channel optical sampler 10 are shown in the embodiment of FIG. 1. This figure depicts an embodiment where the spectroscopic sampler 10 uses discrete pseudo-monochromatic light sources 30, 50. Other embodiments could use lasers or light sources having multiple wavelengths. In this figure, a first light source 30 emits light that passes through the optical interface region and into the biological sample 120. The biological sample 120 can be, for example, a portion of a finger, a hand, an arm, an earlobe, or any other body part. In the diffuse reflectance configuration shown, a portion of the light will be scattered by the tissue in such a way that it passes back through the optical interface region and is detected by a first detector 20. Similarly, another portion of the light emitted by the first source 30 is seen by a second detector element 40. Likewise, light from a second source 50 can also be detected by the first and second detectors 20, 40 after passing through the interfaces and tissue 120. Alternatively, the light sources 30, 50 and detectors 20, 40 can be arranged in a transmission configuration with the light sources 30, 50 on one side of a narrow piece of tissue 120 and the detectors 20, 40 on the other side such that the sources generally face the detectors with the narrow piece of tissue 120 in the middle.

In general, the light sources 30, 50 are controlled in some manner to ensure that the light from individual sources can be measured separately. This can be accomplished by turning-on each source point 30, 50 individually while separately recording all detector readings or encoding them in some fashion so their individual response functions can be separated out after detection. Encoding schemes such as Hadamard encoding or Fourier encoding or others known to one of skill in the art are suitable for this purpose.

The trajectories of individual photons through the tissue 120 appear random due to optical scattering. However, the mean optical path of the detected photons for any source-detector pair is generally a well-behaved and smooth curve. An example of this curve is a first path 110 relating to the first source 30 and the first detector 20. Also shown is a second path 100 between the first source 30 and the second detector 40, a third path 70 between the second source 50 and the second detector 40, and a fourth path 80 between the second source 50 and the first detector 20.

There are small regions 60, 90, 130, 140 that lie between each source 30, 50 or detector 20, 40 and the biological sample 120. These regions 60, 90, 130, 140 are used in the subsequent analysis to model effects at the optical interface, such as contamination and optical coupling effects, and develop a sampler configuration that allows a compensation for the optical artifacts associated with the small regions 60, 90, 130, 140. The small regions are models for the artifacts for the optical interface.

This embodiment provides a means for cross-measurement between different sources 30, 50 and detectors 20, 40 (i.e. each source is "seen" by multiple detectors and each detector "sees" multiple sources). There are many benefits associated with this sampling characteristic, some of which are shown in the following analysis. For simplicity, assumptions are made that the tissue 120 is homogeneous and the light sources 30, 50 are the same wavelength of light, although the basic concept is easily extended by those skilled in the art to non-homogeneous tissue and sources with a plurality of wavelengths. In this embodiment, the absorbance (log-intensity) value, $M_{ijk}$, associated with the $j^{th}$ detector seeing the $i^{th}$ source through the $k^{th}$ sample can be approximated by the below Equation 1:

$$M_{ijk} = \sigma_{si} + p_{ij}A_k + \sigma_{dj} \tag{1}$$

where:
$\sigma_{si}$=optical interface noise at source i due to interface artifacts
$\sigma_{dj}$=optical interface noise at detector j due to interface artifacts
$p_{ij}$=optical pathlength between source i and detector j through the sample
$A_k$=absorbance of the $k^{th}$ tissue sample Each pair of a point light source and a point detector (or a point light source with a concentric ring detector, or a point detector with a concentric ring source, or any other equivalent geometry) will produce measurement data that include interface artifacts from the sampler interface between biological sample 120 and the spectroscopic sampler 10. Thus a particular source-detector pair, where both the source and detector are designated with subscript number 1 in the below Equation 2, produces a measurement, M, for a single wavelength in accordance with Equation 1:

$$M_{11k} = \sigma_{s1} + p_{11}A_k + \sigma_{d1} \tag{2}$$

It is apparent from Equation 2 that the measured data from just a single pair of a first source and a first detector is ambiguous with respect to the portion of the measured signal that originates in the actual tissue, corresponding to the term $p_{11}A_k$, as opposed to noises at the interface of the source and skin, $\sigma_{s1}$, or detector and skin, $\sigma_{d1}$. The measurement corresponds to a single equation with three unknown terms, which is mathematically underdetermined without more information. The goal of most spectral measurements is to measure the tissue absorbance with a minimal amount of interferences, which the optical interface noise at the source and detector represent. In the case of a system that consists solely of a single source-detector pair providing measurement data as in Equation 2, the noise terms are commonly reduced by taking multiple measurements and averaging them together, or by changing the sampling protocol to reduce the magnitude of the noise terms for each measurement, or by examining data for multiple wavelengths each of a form similar to Equation 2, but different (and complimentary) due to the complex interactions of different wavelengths with tissue and at the optical interfaces, or a combination of any of the above. However, these means of generating improved spectral data are usually inadequate, costly, impractical or otherwise difficult to implement for many measurement applications.

The present invention provides for a sampler that has multiple source-detector pairs producing multiple measurements according to Equation 1. The specification for each light source is the same or similar in this embodiment. Often a specification of a light source will give a range of possible wavelengths for a spectral luminescence specification. The actual light sources should emit radiation in the range of wavelengths, but may not be exactly the same wavelengths. The actual light sources could be screened to more closely match each other or could be bought in batches produced similarly so as to likely have closer matching tolerances. In the case of the sampler shown in FIG. 1, there are four distinct measurements provided:

$$M_{11k} = \sigma_{s1} + p_{11}A_k + \sigma_{d1} \tag{3a}$$

$$M_{12k} = \sigma_{s1} + p_{12}A_k + \sigma_{d2} \tag{3b}$$

$$M_{21k} = \sigma_{s2} + p_{21}A_k + \sigma_{d1} \tag{3c}$$

$$M_{22k} = \sigma_{s2} + p_{22}A_k + \sigma_{d2} \tag{3d}$$

These measurements are produced with two sources and two detectors, more specifically, Equation 3a represents a measurement between a first source and a first detector, Equation 3b represents a measurement between the first source and a second detector, Equation 3c represents a measurement between a second source and the first detector, and Equation 3d represents a measurement between the first source and the second detector. Equations 3a-d can be algebraically combined to compensate for the interface noise terms and isolate the absorbance, $A_k$, which is the term of interest, as shown in Equations 4a and 4b below:

$$M_{11k} - M_{21k} = \sigma_{s1} + p_{11}A_k + \sigma_{d1} - (\sigma_{s2} + p_{21}A_k + \sigma_{d1}) = \sigma_{s1} - \sigma_{s2} + (p_{11} - p_{21})A_k \tag{4a}$$

$$M_{12k} - M_{22k} = \sigma_{s1} + p_{12}A_k + \sigma_{d2} - (\sigma_{s2} + p_{22}A_k + \sigma_{d2}) = \sigma_{s1} - \sigma_{s2} + (p_{12} - p_{22})A_k \tag{4b}$$

which leads to Equation 5:

$$(M_{11k} - M_{21k}) - (M_{12k} - M_{22k}) = [(p_{11} - p_{21}) - (p_{12} - p_{22})]A_k \tag{5}$$

Therefore Equation 6:

$$A_k = (M_{11k} + M_{22k} - M_{21k} - M_{12k})/(p_{11} + p_{22} - p_{21} - p_{12}) \tag{6}$$

has isolated the term of interest, $A_k$.

In order to explicitly solve for the absorbance term in Equation 5, the four optical path length terms, $p_{ij}$, should be both known and mathematically well behaved. However, for most spectroscopic applications only the relative path lengths are used since the scale factor, if needed, can be determined experimentally. The optical path lengths are a function of the layout of the sampler as well as the optical properties of the sample being measured. For a particular class of sample, the optical path lengths will be related to the separation between the source and detector. As such, the relative optical paths can be estimated as the linear distance between the associated source-detector pairs. Alternatively, the relative optical paths can be measured by placing a standard sample with a fixed amount of component with a well-defined spectral feature on the sampler. A direct measurement of the size of this feature for each measurement will be proportional to the optical path length for each source-detector pair. Once the configuration of the sampler 10 and the type of biological sample is known, the various path lengths are considered constants.

In general, however, the explicit determination of the absorbance term $A_k$ and the corresponding desire to explicitly determine the optical path lengths, $p_{ij}$, can be eliminated by using standard soft modeling techniques. These techniques are based on the collection of a set of calibration data using a sufficient number of samples with the property of interest (e.g. amount of a spectroscopic analyte in the case of a quantitative estimation task, the disease state in the case of a classification task, or the identity in the case of a biometric task) well-defined as "reference values." The measured calibration data and the associated reference values can then be used to train one or more of a number of different soft-modeling algorithms such as partial least squares, neural networks, principle component regression, linear regression linear or quadratic discriminant analysis, or others as known to one of skill in the art. In this way, the path lengths and other scale factors implicit in the system are estimated by the algorithm and can then be applied to subsequent measurement tasks.

While the example above was based on a sampler consisting of two sources of substantially the same wavelength characteristics and two detectors, additional sources and/or detectors can be included to further enhance the information content of the resulting measurement data. One of skill in the art can appreciate that additional sources of substantially similar wavelength characteristics and/or detectors included in the sampler can generate additional complementary data of the form given in Equation 1. As well, if more than one type of source (i.e. wavelength and/or spectral luminescence specification) is present in the system, then the present invention can be applied to each type of source and the resulting data from each collection of monochromatic sources and detectors can be combined to produce a polychromatic spectrum which can be operated on using the aforementioned algorithms or others know to one of skill in the art. In the polychromatic case, the plurality of detectors may be either the same for each type of source or they may be different.

The present invention provides for an optical measurement capability in which interface noise terms can be better estimated and/or compensated for with a sampler arrangement with multiple sources and detectors incorporating cross-channel measurement ability. This improvement is present in a monochromatic framework but will also augment and improve the performance of a polychromatic spectral system. As well, the resulting measurement data from a cross-channel sampler according to the present invention can be used effectively with a variety of processing methodologies including many hard-modeling and soft-modeling techniques for quantitative measurements and classification tasks as known to one of skill in the art.

In one embodiment of a sampler 10, multiple measurements using the above equation can be collected for a given insertion of the tissue sample 120. The multiple measurements will provide enough information to reduce or remove the effect of artifacts in the optical interface at each of the source and detector locations. The new spectral information is used by standard processing algorithms to improve overall measurement performance of the spectroscopic system.

Figure 2:
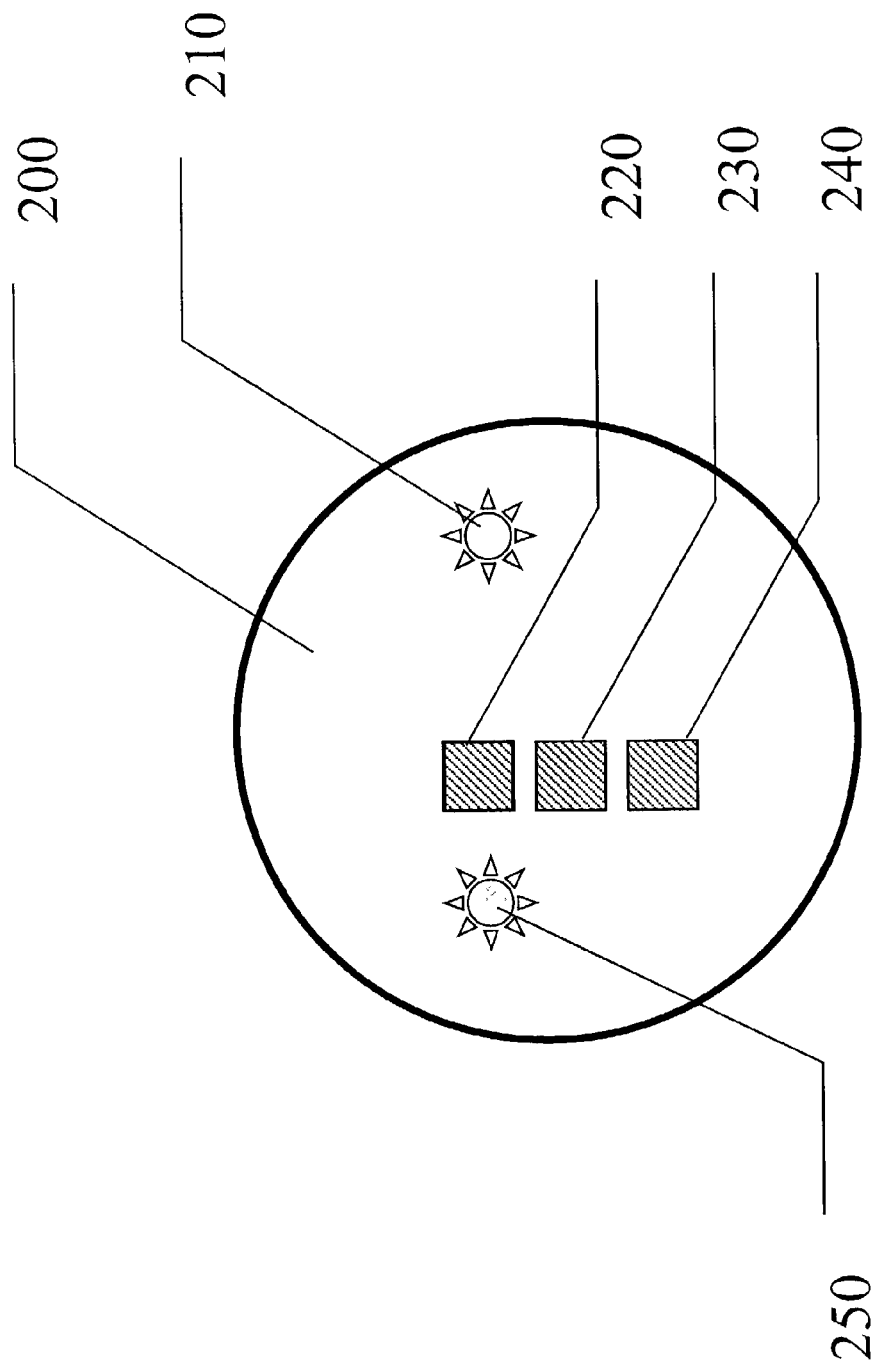
FIG. 2 is a drawing of the top plan view of an embodiment of a cross-channel sampler configuration for a single wavelength.

With reference to FIG. 2, a top view of a sampler 200 having two sources 210, 250 and three detectors 220, 230, 240 is shown. The total measurement, $T_k$, of the $k^{th}$ sample made on this sampler for all combinations of sources and detectors can be described in Equation 7 as:

$$T_k = [M_{11k}; M_{12k}; M_{13k}; M_{21k}; M_{22k}; M_{23k}] \quad (7)$$

where the individual monochromatic measurements are defined as in Equation 1 and can be appended together into a vector of measurements. This vector can then be presented to standard processing algorithms such as linear discriminant analysis (LDA) for classification or partial least squares (PLS) for quantitative measurements, as well as techniques and algorithms such as neural nets, quadratic discriminant analysis (QDA), Bayesian estimation, principle component regression (PCR), linear and nonlinear regression, multiple least squares (MLS), and many others also known to one of skill in the art. The maximum number of measurements is equal to the number of sources multiplied by the number of detectors. This maximum number is reduced to eliminate source/detector pairs that don't produce a usable signal for whatever reason.

Figure 3:
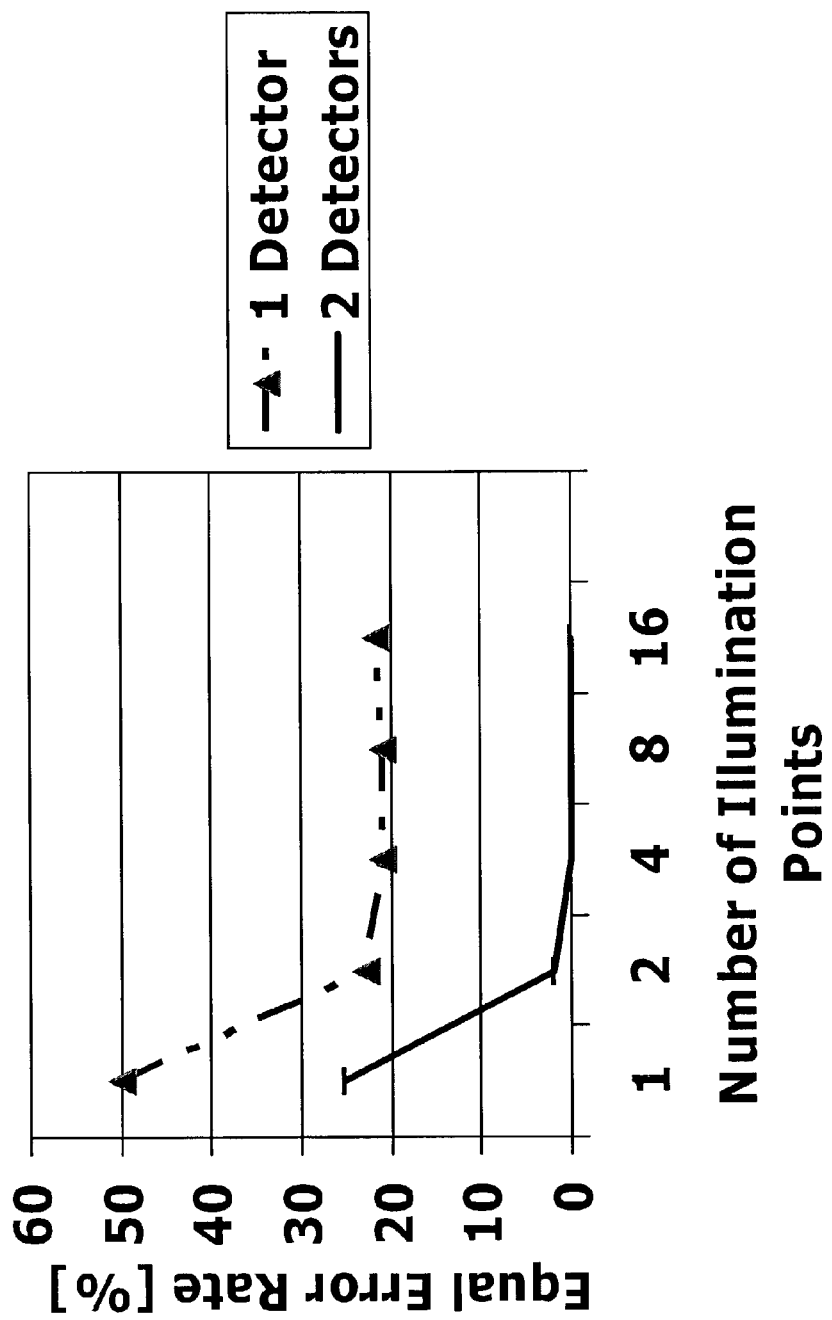
FIG. 3 is a graph of results of an embodiment of a simulation of various spectroscopic sampler arrangements used for biometric verification.

Referring next to FIG. 3, the results are shown of a monochromatic simulation of different samplers 10 used to collect data that is then used for a biometric verification task. The data were generated using Equation 1 and the algorithm used for this classification example was an implementation of LDA as implemented in MatLab™ version 6.1 (i.e., using the "classify.m" routine) available at MathWorks.com. The pathlengths of associated sources and detectors varied randomly between 1.0 and 1.5 units in length. The resulting Equal Error Rate (EER) is plotted as a function of the number of source points for both an embodiment with a single detector and for an embodiment with two detectors. The figure shows that the dual sources combined with multiple detectors in one embodiment with cross-channel measurement capability produces greatly improved results relative to the single-detector embodiment. Embodiments having even greater numbers of sources also produce improved results relative to the single-detector, multiple sources, embodiment.

Figure 4:
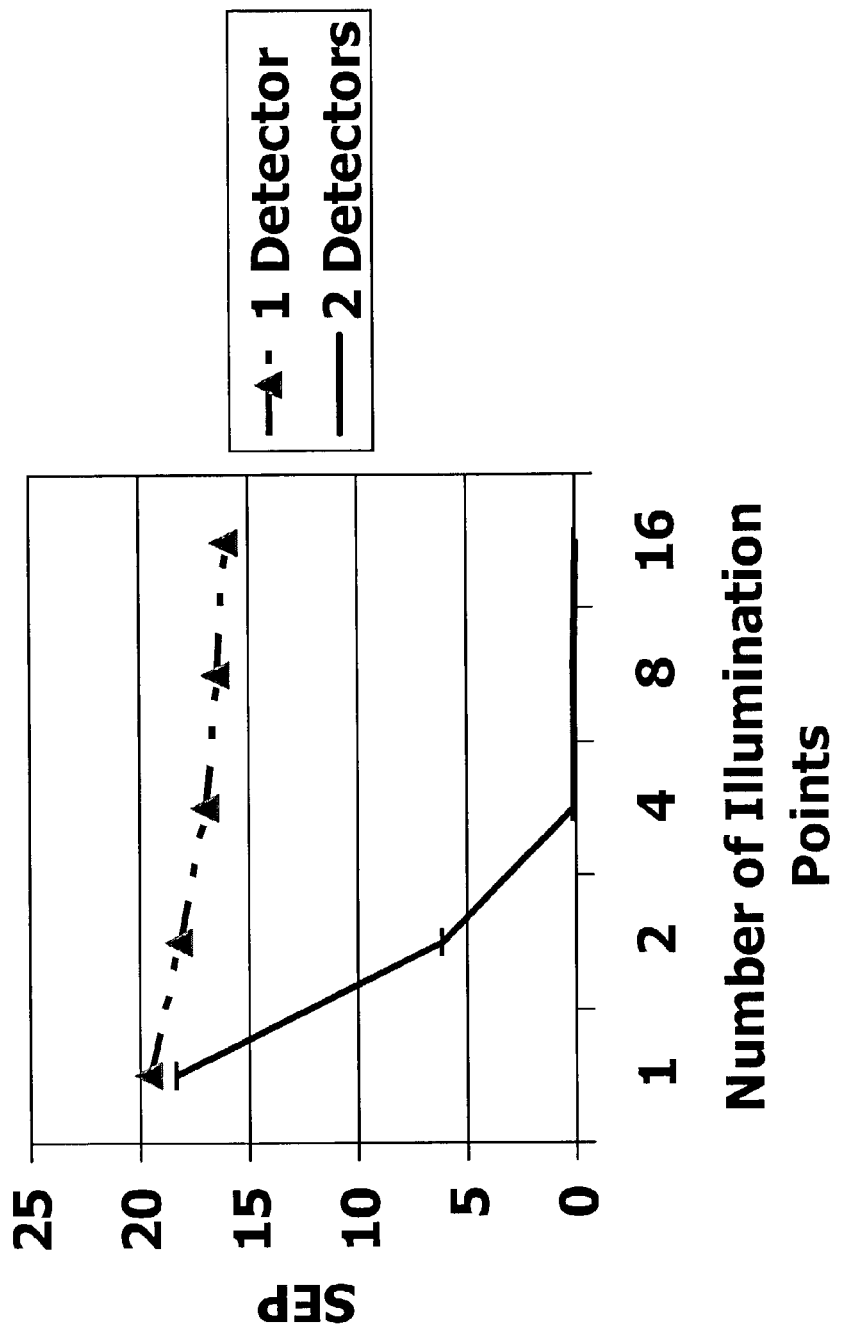
FIG. 4 is a graph of results of an embodiment of a simulation of various spectroscopic sampler arrangements used for quantitative determinations.

FIG. 4 shows the results of an embodiment of a simulation like that done for FIG. 3, but in this embodiment, the data are used for a quantitative determination such as noninvasive glucose monitoring, oxygenation saturation measurements, noninvasive alcohol measurements, and other measurements. The algorithm used for this simulation embodiment is PLS. The metric shown in the FIG. 4 is Standard Error of Prediction (SEP), which is approximately equal to the root-mean-square (RMS) error of the predictions relative to the true analyte values that were simulated. As with the case of biometric determinations (e.g., FIG. 3), the SEP is seen to improve only slightly in an embodiment where one or more sources are measured by a single detector. Significantly improved performance improvements occur when two or more detectors are used to collect data from multiple sources as taught herein.

Figure 5:
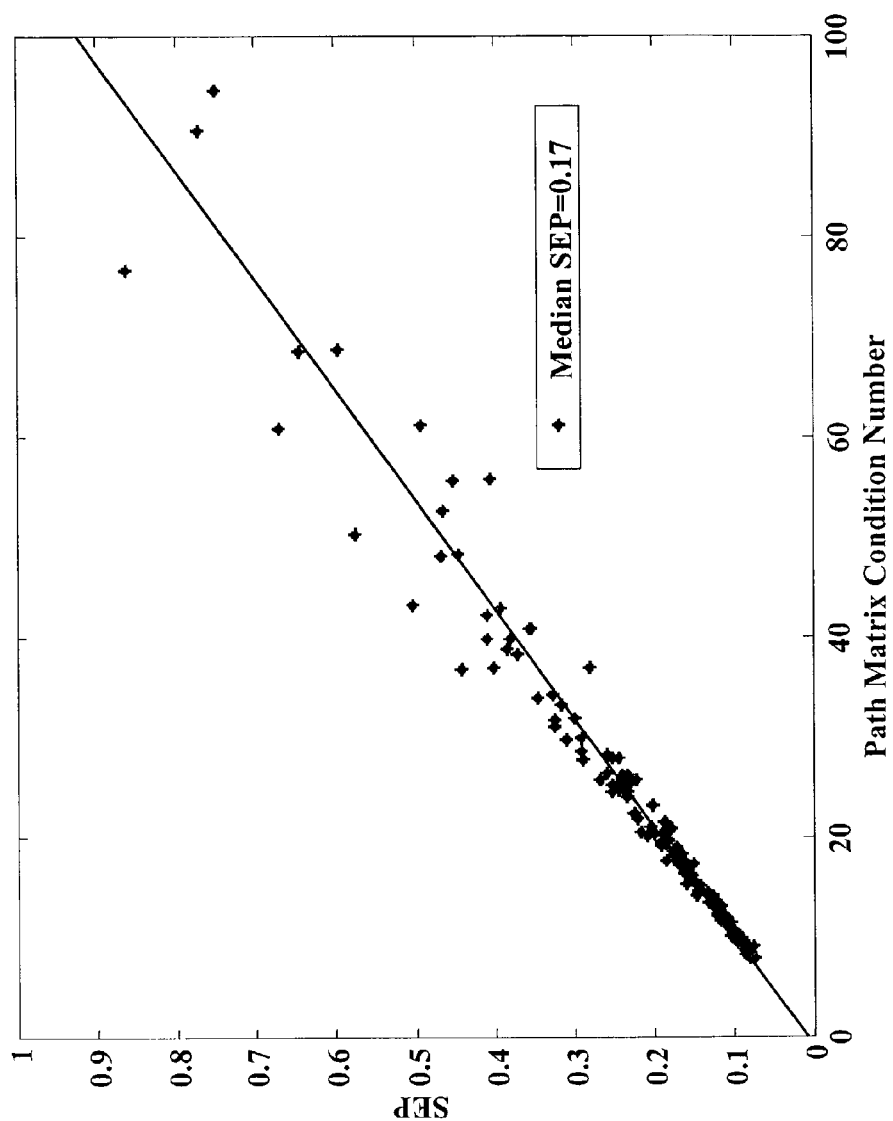
FIG. 5 is a graph of performance of the quantitative simulation data as a function of the condition number of the pathlength matrix of one embodiment.

FIG. 5 shows an example of the effect of the choice of the pathlength relationships between the various sources 30 and detectors 20, which is a function of the sampler design as well as the optical properties of the tissue 120 being measured. Multiple realizations of the simulation were run choosing random relationships between the sources 30 and detector 20. The condition number of the resulting pathlength matrix with elements $p_{ij}$ (as given in Equation 1) is calculated using the "cond.m" function in MatLab™ version 6.1, where a smaller condition number corresponds to a better conditioned system. FIG. 5 shows the SEP as a function of the pathlength matrix condition number, which tends to show that a better-conditioned pathlength matrix produces better results. This finding, in turn, can provide design guidance for the sampler geometry: a sampler that corresponds to a well-conditioned pathlength matrix can perform better than one with a less well-conditioned matrix. As a first approximation, the pathlength matrix can be said to be proportional to the linear distance between the source and detector points at the optical interface (for a planar sampler). Those skilled in the art can make further refinements to this approximation by knowing or modeling the optical properties of the biological sample 120 being measured as well as the specific sampler 10 geometry.

Figure 6:
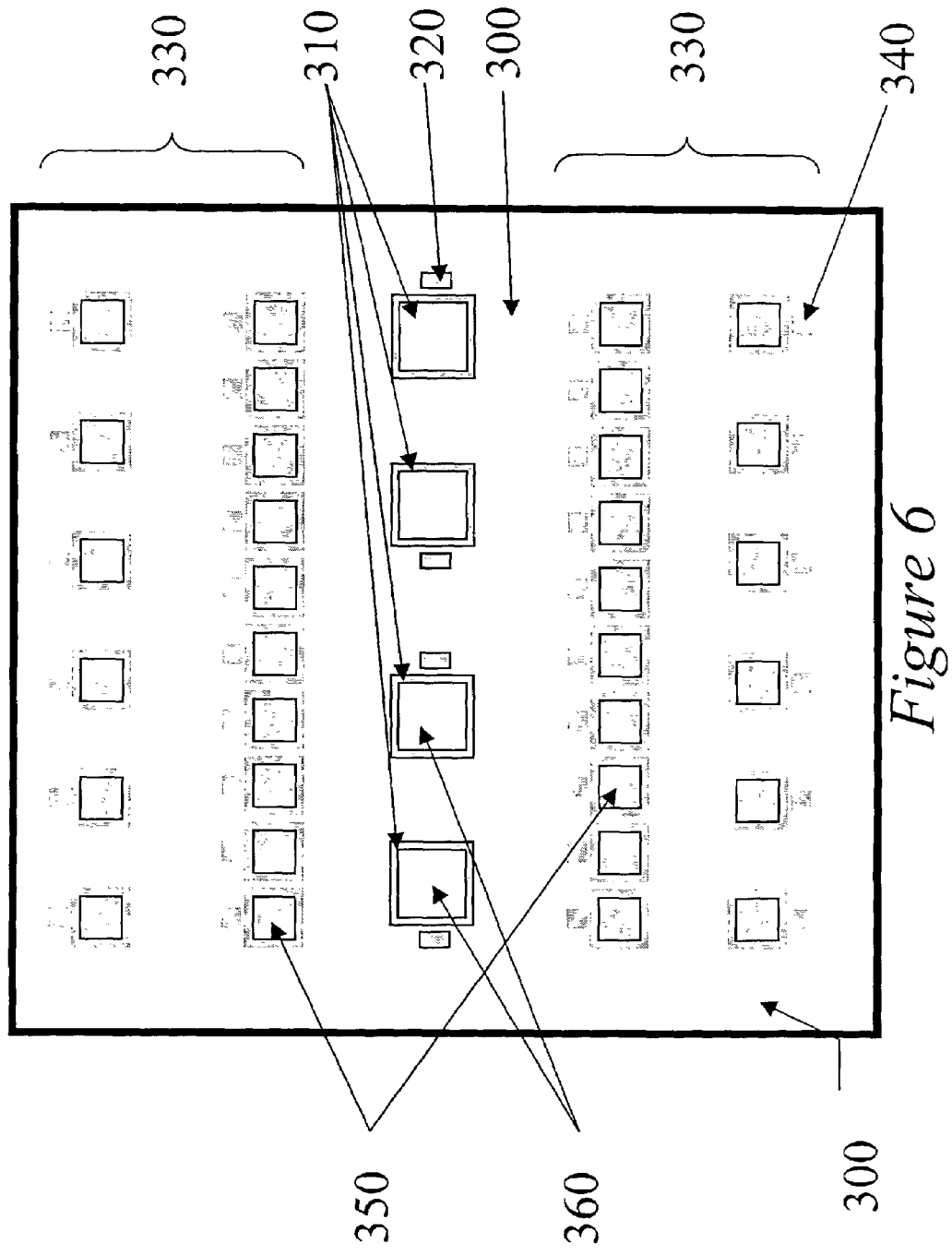
FIG. 6 is a layout of a top plan view of an embodiment of a cross-channel sampler including 32 LED die and 4 detector elements.

FIG. 6 shows a diagram of an embodiment of a sampler 300 consisting of multiple LEDs 330 of various colors and four detectors 310. In this embodiment, the LED die 330 are electrically coupled by a bonded wire (not shown) to a respective bond pad 340. Similarly, the photodiode detector die 310 are electrically coupled to respective bond pads 320. In the sampler 300, there are two or three LEDs of each of the 14 different LED types (i.e., nominally the same central wavelengths). For example, LED die 350 have the same central wavelength that is a different wavelength than other die in the collection of LED die 330. In this embodiment, the wavelengths of the various LED dice 330 vary from 390 nm to 940 nm. The number and configuration of detectors 310 was selected in this embodiment to ensure that each pair of same wavelength LEDs would be seen by at least two detectors given the relatively short pathlengths through tissue that some of the LEDs have (e.g. 390 nm). In these embodiments, at least two detectors will effectively "see" an appreciable amount of light from each of the LED's of a certain type after passing through the tissue 120, as taught in this invention. For example, signals from LED pair 350 are seen by at least a pair 360 of detectors 310. In an embodiment using longer wavelengths such as 940 nm, which has very long penetration depths through tissue, all four detectors could see a measurable amount of light. Measurements made from all of the detector-LED combinations (or just those in which the optical signal is significant) can be combined together as a spectrum and operated on in any of the manners taught in this invention or known to one of skill in the art.

The method of noninvasive illumination and sensing disclosed in this invention can be implemented using a variety of different hardware implementations. In embodiments where small pseudo-monochromatic point sources are available, they can be directly incorporated in the sampler. Examples of sources in this category include solid-state LED's, organic LED's, polymer LED's, laser diodes, vertical-cavity surface emitting lasers (VCSEL's), quantum dots, and other similar illumination sources. The sources can be bare die as discussed or they can be in other forms such as a variety of packages. Methods of electrically and mechanically attaching the sources can also differ substantially depending on the particular packaging, configuration and intended use of the sensor. As well, rather than using solid-state sources, optical filters can be combined with broadband sources such as incandescent bulbs to provide pseudo-monochromatic point sources.

The detectors of various embodiments can either be discrete elements such as photodiodes, or can be one- or two-dimensional arrays. In either embodiment, detector types include silicon, InGaAs, InSb, germanium, MCT, bolometers, and other choices known to one of skill in the art.

In some embodiments it may not be practical or desirable to have the source and/or detector elements located directly in the sampler. In these embodiments, optics such as optical fibers, lightpipes, lenses and other optical elements can be used to separate the sources and/or detectors from the sampler itself as well as to provide space between the different components. For simplicity, the present description uses the term 'fiber' to refer to this entire set of implementation alternatives.

Figure 7:
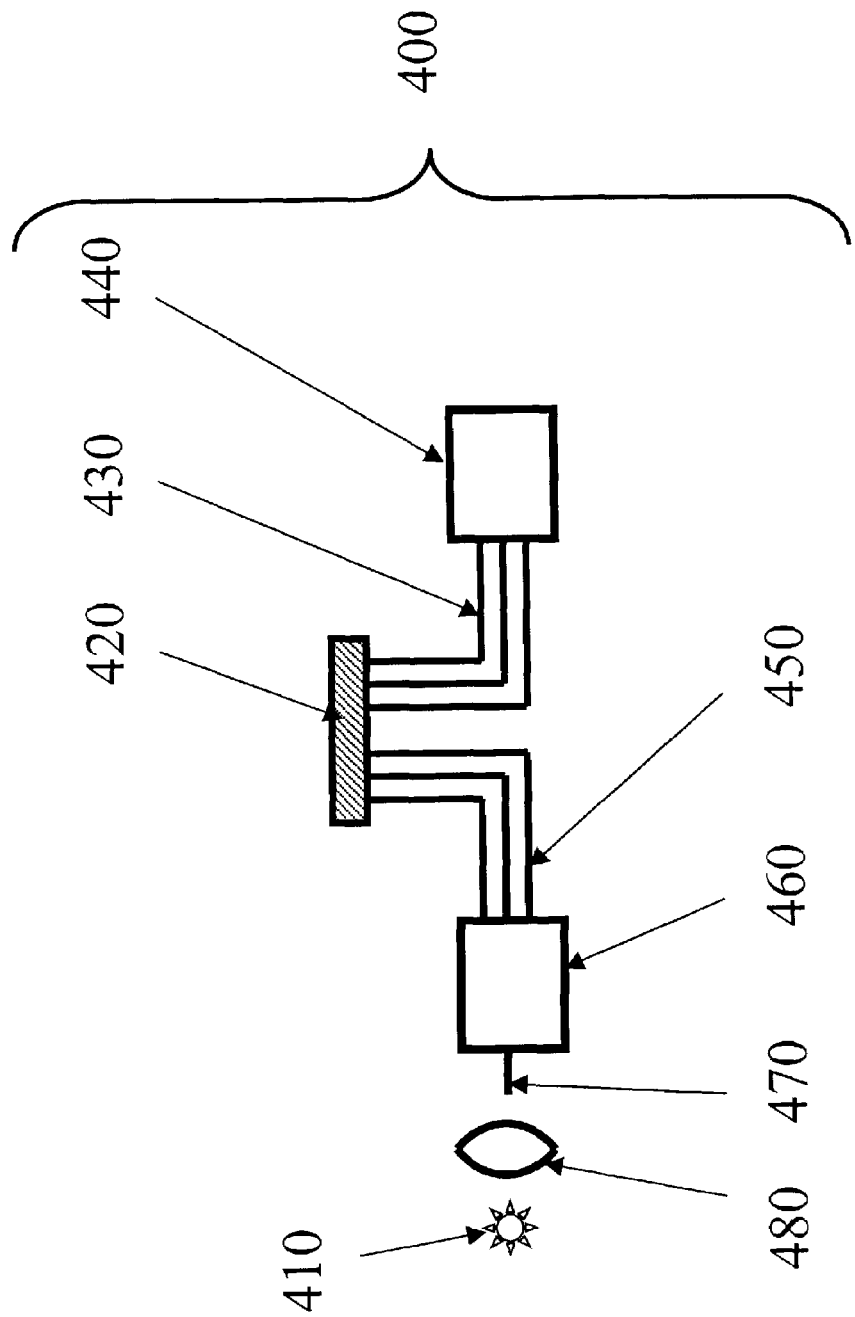
FIG. 7 is a block diagram of an embodiment of a cross-channel sampler implemented with optical fibers.

One embodiment of a fiber-based sampler is shown in FIG. 7. The spectroscopic sensor 400 is comprised of a broad-band light source 410, focusing optics 480 to image the source into input fiber 470. Input fiber 470 then goes to an optical switch 460 that illuminates one or some combination of illumination fibers 450, which are routed to a sampler surface 420 that has a configuration suitable for cross-channel sampling, as described above. The biological sample 120 is placed upon the sampler surface 420 for measurement. A collection of output fibers 430 collect light from the tissue 120 that has been place on the surface 420 of the sampler and route the light to spectrometer 440.

The broad-band light source 410 can be an incandescent source such as a quartz-tungsten-halogen bulb or a glowbar or other heated element, or can be a solid-state element such as white-light LED, or can be a combination of different sources of different types and/or wavelength characteristics. The optical switch 460 can be based on a mirror whose position is controlled by a galvanometer, a microelectromechanical system (MEMS) consisting of mirrors or variable apertures, a spatial modulator using liquid crystals or other means, a waveguide-switch, or one of a large number of other methods known to one of skill in the art.

The spectrometer 440 can be one of a large number of alternatives. The spectrometer 440 can be a Fourier Transform infrared (FTIR) system, a grating-based system (array or scanning), a Hadamard spectrometer, a mock spectrometer, a Sagnac spectrometer, a refractive spectrometer such as a prism-based system, an optical filter based device, an acousto-optical tunable filter, or other variants as known to one of skill in the art. In addition, a spectrometer such as an FTIR could be separated into the interferometer portion and the detector, and the interferometer could be positioned elsewhere in the system such as before or after the optical switch 460.

Figure 8:
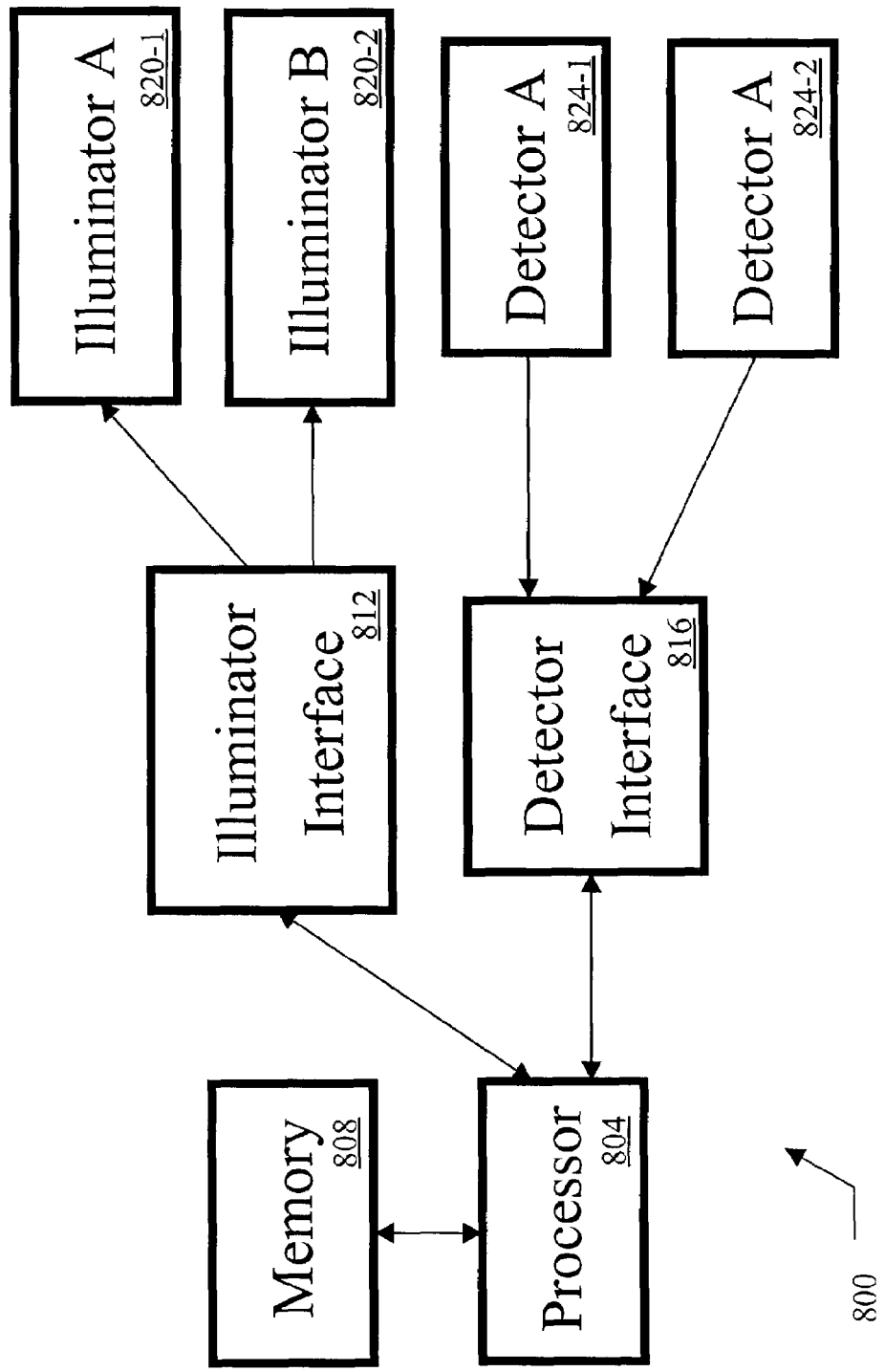
FIG. 8 is a block diagram of an embodiment of a sampling system.

With reference to FIG. 8, a block diagram of an embodiment of a sampling system 800 is shown. This embodiment includes two illuminators 820 and two detectors 824, although other embodiments could have more of each. Included in the sampling system 800 are a processor 804, memory 808, an illuminator interface 812, a detector interface 816, a first illuminator 820-1, a second illuminator 820-2, a first detector 824-1, and a second detector 824-2.

The processor 804 manages operation of the sampling system 800. A memory 808 is used by the processor 804 to store software and data. The memory could include volatile and non-volatile portions. Configuration data is sent by the processor 804 to the illuminator interface 812 to cause the illumination. The measurable radiation is read back from the detector interface 816 by the processor 804.

The processor 804 could also do processing on the information from the detector interface 816 for a variety of purposes. The measurements could be used in a biometric determination such a one-to-many identification and/or a one-to-one verification. Additionally, the measurements could be used in a sample liveness verification, a sample authenticity verification, a gender estimation, an age estimation, and/or to otherwise classify the physiological state of the tissue. In one example, the measurements could be used to detect or confirm the presence of cancer. Measurements could also be used to estimate the amount of analytes present in the tissue such as glucose, alcohol and/or hemoglobin.

The measurements from the detector interface 816 could be analyzed by the processor 804 in a number of ways. A classification algorithm or a quantitative estimation algorithm could be used, for example. Examples of classification algorithms include a discriminant analysis, a clustering analysis, a partial least squares calculation, a regression, a neural network, a classification tree, and/or a support vector machine. Examples of quantitative estimation algorithms include a partial least squares calculation, a multiple least squares, a regression, and/or a neural network. The measurement values could be matched against predetermined values or could be checked against a threshold value.

The illuminator interface 812 configures the illuminators 820 under the command of the processor 804. Digital information from the processor 804 is converted by the illuminator interface to activate the illuminators. The processor 804 can activate the individual illuminators 820 through this interface 812. For example, the processor could activate the illuminators sequentially without overlap, sequentially with overlap, or according to some other encoding sequence. In some cases, the illuminators 820 are sufficiently separated from each other such that two or more can be illuminated simultaneously. Different wavelength illuminators can be combined with detectors that have different wavelength response characteristics to differentiate illuminators that are active at the same time.

In some embodiments, the illuminator interface 812 could include a light source with optical fibers coupled to the illumination points 820. Light valves or other switches could be used to activate individual illumination points 820. Filters could be used to divide a broadband light source into different wavelengths for the various illumination points 820. In some cases, different wavelengths could be sequentially sent down the fibers to allow an illumination point 820 to operate at different wavelengths. Filters could be integrated into the illumination points 820 of other embodiments. The illuminators 820 could include solid-state electro-optical components such as a light emitting diode, a laser diode, a vertical cavity surface emitting laser, and/or a quantum dot laser.

The detector interface 816 does any biasing or configuration to the detectors 824 and converts measurement signals from the detectors 824 into digital form. Those digital values are read by the processor 804. The detector interface 816 can deactivate the detectors 824 when not in use. The detectors 824 may be tunable to a given wavelength using filters, for example, to only read wavelengths from a particular illuminator 820. The detector could be optically coupled to detection points 824 in some embodiments such that the radiation is actually read at the detector interface 816. The detectors 820 could be arranged as part of a one or two dimensional array of detectors.

A number of variations and modifications of the invention can also be used. For example, some embodiments could eliminate the absorbance value when outside a predetermined range of values. If there was excessive optical interference noise or inadequate biologic sample, a particular reading from a source/detector pair could be ignored. This could compensate for the sampler being too dirty or the tissue not properly contacting the sampler. Some embodiments use separate die that are bonded together to form the sampler. Other embodiments could use a sampler that is formed homogeneously on the same substrate.

While the principles of the invention have been described above in connection with specific apparatuses and methods, it is to be clearly understood that this description is made only by way of example and not as limitation on the scope of the invention.

What is claimed is:

1. A sampling system for spectroscopic measurements of a biological sample, the sampling system comprising:
    a plurality of illumination points;
    a plurality of detection points, wherein:
    each of the plurality of illumination points is involved in at least two measurements of illumination through the biological sample, and
    each of the plurality of detection points is involved in at least two measurements of illumination through the biological sample;
    a memory for storing a plurality of measurements, each of the measurements including information defining a combination of a particular one of the plurality of illumination points and a particular one of the plurality of detection points involved in the each of the measurements; and
    a processor configured to determine a value from the plurality of measurements that is related to the biological sample by compensating for interface noise terms from the combinations of particular ones of the plurality of illumination points and particular ones of the plurality of detection points.

2. The sampling system for spectroscopic measurements of the biological sample as recited in claim 1, wherein the value is compared with other values to determine characteristics of the biological sample.

3. The sampling system for spectroscopic measurements of the biological sample as recited in claim 1, wherein the value is compared with other values to authenticate an identity belonging to the biological sample.

4. The sampling system for spectroscopic measurements of the biological sample as recited in claim 1, wherein the value is compared with a threshold to determine characteristics of the biological sample.

5. The sampling system for spectroscopic measurements of the biological sample as recited in claim 1, wherein the value is compared with a threshold to authenticate an identity belonging to the biological sample.

6. The sampling system for spectroscopic measurements of the biological sample as recited in claim 1, wherein the processor explicitly solves for the value.

7. The sampling system for spectroscopic measurements of the biological sample as recited in claim 1, wherein the plurality of illumination points numbers two.

8. The sampling system for spectroscopic measurements of the biological sample as recited in claim 1, wherein the plurality of detection points numbers two.

9. The sampling system for spectroscopic measurements of the biological sample as recited in claim 1, wherein:
    the plurality of illumination points includes a first illumination point and a second illumination point;
    the first illumination point has a similar spectral luminescence specification than the second illumination point.

10. The sampling system for spectroscopic measurements of the biological sample as recited in claim 1, wherein the value is used in a biometric determination.

11. The sampling system for spectroscopic measurements of the biological sample as recited in claim 10, wherein said biometric determination is at least one of the following:
    a one-to-many identification,
    a one-to-one identity verification,
    a sample liveness verification,
    a sample authenticity verification,
    a gender estimation, and
    an age estimation.

12. The sampling system for spectroscopic measurements of the biological sample as recited in claim 1, wherein the value represents an analyte measurement.

13. The sampling system for spectroscopic measurements of the biological sample as recited in claim 12, wherein the analyte measurement is of at least one of:
    glucose,
    alcohol, and
    hemoglobin.

14. The sampling system for spectroscopic measurements of the biological sample as recited in claim 1, wherein the value relates to a classification of physiological state of the tissue.

15. The sampling system for spectroscopic measurements of the biological sample as recited in claim 14, wherein the classification of physiological state of the tissue is a determination of the presence of cancer.

16. The sampling system for spectroscopic measurements of the biological sample as recited in claim 1, wherein at least one of the plurality of detection points receives illumination from each of the plurality of illumination points in a manner that allows the illumination from each of the first and second illumination points to be separately analyzed.

17. The sampling system for spectroscopic measurements of the biological sample as recited in claim 1, wherein the plurality of illumination points are illuminated by using an encoding pattern.

18. The sampling system for spectroscopic measurements of the biological sample as recited in claim 1, wherein at least one of the plurality of detection points includes a discrete detector element.

19. The sampling system for spectroscopic measurements of the biological sample as recited in claim 1, wherein at least some of the plurality of detection points are arranged in a linear detector array.

20. The sampling system for spectroscopic measurements of the biological sample as recited in claim 1, wherein at least some of the plurality of detection points are arranged in a two-dimensional detector array.

21. The sampling system for spectroscopic measurements of the biological sample as recited in claim 1, wherein the plurality of illumination points include solid-state electro-optical components.

22. The sampling system for spectroscopic measurements of the biological sample as recited in claim 21, wherein the solid-state electro-optical components include at least one of:
    a light emitting diode,
    a laser diode,
    a vertical cavity surface emitting laser, and
    a quantum dot laser.

23. A method of performing spectroscopic determinations on a biological sample, the method comprising steps of:
    providing a plurality of illumination points;
    providing a plurality of detection points;
    measuring illumination incident on each of the plurality of detection points a plurality of times, wherein the measuring steps produce a plurality of measurements, each of the measurements including information defining a combination of a particular one of the plurality of illumination points and a particular one of the plurality of detection points involved in the each of the measurements; and
    determining a value for the biological sample from the plurality of measurements, comprising compensating for interface noise terms from the combinations of particular ones of the plurality of illumination points and particular ones of the plurality of detection points.

24. The method of performing spectroscopic determinations on the biological sample as recited in claim 23, further comprising a step of analyzing the value in a biometric determination.

25. The method of performing spectroscopic determinations on the biological sample as recited in claim 24, wherein said biometric determination is at least one of:
    a one-to-many identification,
    a one-to-one identity verification,
    a sample liveness verification,
    a sample authenticity verification,
    a gender estimation, and
    an age estimation.

26. The method of performing spectroscopic determinations on the biological sample as recited in claim 23, wherein the value relates to an analyte measurement.

27. The method of performing spectroscopic determinations on the biological sample as recited in claim 26, wherein the analyte measurement is of at least one of:
    glucose,
    alcohol, and
    hemoglobin.

28. The method of performing spectroscopic determinations on the biological sample as recited in claim 23, wherein the determining step includes performing a classification algorithm.

29. The method of performing spectroscopic determinations on the biological sample as recited in claim 28, wherein the classification algorithm includes at least one of:
    a discriminant analysis,
    a clustering analysis,
    a partial least squares calculation,
    a regression,
    a neural network,
    a classification tree, and
    a support vector machine.

30. The method of performing spectroscopic determinations on the biological sample as recited in claim 23, wherein the determining step includes performing a quantitative estimation algorithm.

31. The method of performing spectroscopic determinations on the biological sample as recited in claim 30, wherein said quantitative estimation algorithm includes at least one of:
    a partial least squares calculation,
    a multiple least squares,
    regression, and
    a neural network.

32. A computer-readable medium having computer-executable instructions for performing the computer-implementable method for performing spectroscopic determinations on the biological sample as recited of claim 23.

33. A sampler for spectroscopic measurements of a biological sample, the sampler comprising:
    a first illumination point that illuminates at least two detection points with measurable radiation;
    a second illumination point that illuminates said at least two detection points with measurable radiation;
    a first of said at least two detection points that receives measurable radiation from said first and second illumination points;
    a second of said at least two detection points that receives measurable radiation from said first and second illumination points, wherein the first illumination point, the second illumination point, the first detection point, the second detection point are configured to operatively engage the biological sample; and
    a controller in communication with the first and second illumination points and in communication with the first and second detection points to generate a plurality of measurements, each of the measurements including information defining a combination of a particular one of the plurality of illumination points and a particular one of the plurality of detection points involved in the each of the measurements, and to determine a value from the plurality of measurements that is related to the biological sample by compensating for interface noise terms from the combinations of particular ones of the plurality of illumination points and particular ones of the plurality of detection points.

34. The sampler for spectroscopic measurements of the biological sample as recited in claim 33, wherein at least one of the first and second detection points receives illumination from each of the first and second illumination points in a manner that allows the illumination from each of the first and second illumination points to be separately analyzed.

35. The sampler for spectroscopic measurements of the biological sample as recited in claim 33, wherein at least one of the first and second detection points are illuminated by using an encoding pattern.

36. The sampler for spectroscopic measurements of the biological sample as recited in claim 33, wherein at least one of the first and second detection points includes a discrete detector element.

37. The sampler for spectroscopic measurements of the biological sample as recited in claim 33, wherein at least one of the first and second detection points is arranged in a linear detector array.

38. The sampler for spectroscopic measurements of the biological sample as recited in claim 33, wherein at least one of the first and second detection points are arranged in a two-dimensional detector array.

39. The sampler for spectroscopic measurements of the biological sample as recited in claim 33, wherein at least one of the first and second illumination points includes a solid-state electro-optical component.

40. The sampler for spectroscopic measurements of the biological sample as recited in claim 39, wherein the solid-state electro-optical component includes at least one of:
   a light emitting diode,
   a laser diode,
   a vertical cavity surface emitting laser
   and
   a quantum dot laser.

* * * * *

UNITED STATES PATENT AND TRADEMARK OFFICE
CERTIFICATE OF CORRECTION

| | | |
|---|---|---|
| PATENT NO. | : 7,613,504 B2 | Page 1 of 1 |
| APPLICATION NO. | : 10/262403 | |
| DATED | : November 3, 2009 | |
| INVENTOR(S) | : Rowe | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1189 days.

Signed and Sealed this

Eleventh Day of January, 2011

David J. Kappos
*Director of the United States Patent and Trademark Office*